United States Patent
Hosoda et al.

(10) Patent No.: US 10,775,241 B2
(45) Date of Patent: Sep. 15, 2020

(54) CORRELATOR WITH A VARIABLE SAMPLING TIME SCHEME

(71) Applicant: Canon U.S.A., Inc., Melville, NY (US)

(72) Inventors: Masaki Hosoda, Cambridge, MA (US); Haruo Nakaji, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 389 days.

(21) Appl. No.: 15/634,825

(22) Filed: Jun. 27, 2017

(65) Prior Publication Data

US 2018/0372544 A1 Dec. 27, 2018

(51) Int. Cl.
| | |
|---|---|
| *G01J 3/457* | (2006.01) |
| *A61B 5/00* | (2006.01) |
| *G01N 15/00* | (2006.01) |
| *G01N 21/64* | (2006.01) |
| *G01J 3/28* | (2006.01) |
| *A61B 5/026* | (2006.01) |

(52) U.S. Cl.
CPC ............ *G01J 3/457* (2013.01); *A61B 5/0075* (2013.01); *A61B 5/7246* (2013.01); *G01N 15/00* (2013.01); *G01N 21/6408* (2013.01); *A61B 5/0261* (2013.01); *G01J 2003/283* (2013.01); *G01N 2015/0003* (2013.01); *G01N 2015/0053* (2013.01)

(58) Field of Classification Search
CPC ... G01J 3/457; G01J 2003/283; A61B 5/0075; A61B 5/7246; G01N 21/6408; G01N 15/0205; G01N 15/0211; G01N 21/6458
See application file for complete search history.

(56) References Cited

U.S. PATENT DOCUMENTS

| | | | |
|---|---|---|---|
| 5,124,551 A | 6/1992 | Urakami et al. | |
| 6,885,448 B2* | 4/2005 | Tsutsui | G01N 15/0211 250/336.1 |
| 7,724,369 B2* | 5/2010 | Yamaguchi | G01N 15/0205 356/336 |
| 8,531,663 B1* | 9/2013 | Tochino | G01N 15/0211 356/336 |
| 9,378,434 B2* | 6/2016 | Suzuki | G06T 5/50 |

(Continued)

FOREIGN PATENT DOCUMENTS

WO 2016164900 A1 10/2016

OTHER PUBLICATIONS

Schatzel, K. et al., "Photon correlation measurements at large lag times: improving statistical accuracy" Journal of Modern Optics, 1988, pp. 711-718, Vo. 35, No. 4.

*Primary Examiner* — Stephanie E Bloss
(74) *Attorney, Agent, or Firm* — Canon U.S.A., Inc., IP Division

(57) ABSTRACT

The present disclosure relates in general to Diffuse Correlation Spectroscopy system for obtaining an autocorrelation function, and more particular, to a correlator and method for controlling a sampling time period and data length used for calculating an autocorrelation function. The correlator may include, a sampling gate circuit which is open during a variable time period and provides a data sample, a correlation circuit which calculates a correlation function from the data sample provided from the sampling gate circuit, and a parameter determining circuit which determines a sampling time period to be used by the sampling gate circuit based on the correlation function.

15 Claims, 5 Drawing Sheets

(56) References Cited

U.S. PATENT DOCUMENTS

| | | | | |
|---|---|---|---|---|
| 2002/0180972 | A1* | 12/2002 | Ansari | G01N 15/0211 |
| | | | | 356/336 |
| 2003/0133110 | A1* | 7/2003 | Tsutsui | G01N 15/0211 |
| | | | | 356/336 |
| 2007/0285308 | A1* | 12/2007 | Bauregger | G01S 19/10 |
| | | | | 342/357.27 |
| 2009/0115658 | A1* | 5/2009 | Zimmerman | G01S 19/11 |
| | | | | 342/357.27 |
| 2015/0124259 | A1* | 5/2015 | An | G01B 9/02047 |
| | | | | 356/456 |
| 2016/0353997 | A1 | 12/2016 | Yodh et al. | |
| 2017/0238878 | A1* | 8/2017 | Lading | A61B 5/726 |
| 2018/0070830 | A1* | 3/2018 | Sutin | A61B 5/0261 |
| 2018/0153439 | A1* | 6/2018 | Miller | A61B 5/7235 |

\* cited by examiner

CORRELATOR WITH A VARIABLE SAMPLING TIME SCHEME

BACKGROUND

Field of the Disclosure

The present disclosure relates in general to Diffuse Correlation Spectroscopy system for obtaining an autocorrelation function, and more particular, to a correlator and method for controlling a sampling time period and data length used for calculating an autocorrelation function.

Description of the Related Art

Diffuse Correlation Spectroscopy or Diffusing Wave Spectroscopy is a useful technology to detect particle motion in the sample using coherent light. The scattered light by particles in a sample is entered in a detector and constructive and destructive interference is observed as speckle. When scattering particles are moving in a sample, speckle intensity detected by a photodiode also fluctuates. By counting photons scattered in the sample, the movement of the scattering particles in a sample can be estimated precisely. The key features of the Diffuse Correlation Spectroscopy technology are a laser, a detector, and a correlator which calculates an intensity autocorrelation function from a fluctuation of photon signals. Calculating the intensity autocorrelation function, also known as $g2(\tau)$, can extract meaningful information such as blood flow in a tissue.

Currently, obtaining such information from a sample requires a technique of using fixed and plural sampling gates which are open synchronously with one another for different periods of time. However, there are issues when using this technique. One issues is the excessive calculation of $g2(\tau)$ because each sampling gate is counting photon signals with associated memories and circuits for calculating $g2(\tau)$. When calculating a $g2(\tau)$ for more time lag region, the required number of gates is increased and many $g2(\tau)$ curves from each gate need to be calculated simultaneously to output a combined $g2(\tau)$ curve. Another issue is in order to calculate the intensity autocorrelation function it requires a large amount of resources and memory for each gate because the autocorrelation is a comparison of an original signal, which needs to be stored in a memory. As such, the current technique requires increased time, resources, and memory in order to obtain and calculate an accurate intensity autocorrelation function.

Thus, there is a need in the art for a correlator using less resources and memory by making the sampling time and the total data length controllable based on a measurement result to accurately achieve the higher output rate of an intensity autocorrelation function, which can be applied to measurements of sample flow and pulsation.

SUMMARY

Disclosed and claimed herein are systems, methods and devices for a Diffuse Correlation Spectroscopy (DCS) system for obtaining an autocorrelation function, and more particular, to a correlator and method for controlling a sampling time period and data length used for calculating an autocorrelation function.

In one aspect of the present disclosure a DCS system includes a system of one or more computers which can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a correlator including, a sampling gate circuit which is open during a variable time period and provides a data sample. The correlator also includes a correlation circuit which calculates a correlation function from the data sample provided from the sampling gate circuit. The correlator also includes a parameter determining circuit which determines a sampling time period to be used by the sampling gate circuit based on the correlation function. Other embodiments of this aspect include corresponding computer systems, apparatus, and computer programs recorded on one or more computer storage devices, each configured to perform the actions of the methods.

Implementations may include one or more of the following features. The correlator where the parameter determining circuit adjusts the variable time period the sampling gate circuit is open based on the determined sampling time period. The correlator where the parameter determining circuit determines the sampling time period based on a decay time calculated from the correlation function. The correlator where the parameter determining circuit determines a data length used to calculate the correlation function, which is based on a decay time calculated from the correlation function. The correlator where the parameter determining circuit has a determination function, which determines if a calculated correlation function is valid or not based on a coherence factor obtained by the correlation function. The correlator where the correlation circuit has a determination function, which determines if a calculated correlation function is valid or not valid based on a plateau level of the correlation function. Implementations of the described techniques may include hardware, a method or process, or computer software on a computer-accessible medium One general aspect includes a method for determining a correlation function by a correlator, the method including, obtaining a data sample from a sampling gate circuit which is open during a variable time period. The method also includes calculating by a correlation circuit a correlation function from the data sample provided from the sampling gate circuit. The method also includes determining by a parameter determining circuit a sampling time period to be used by the sampling gate circuit based on the correlation function. Other embodiments of this aspect include corresponding computer systems, apparatus, and computer programs recorded on one or more computer storage devices, each configured to perform the actions of the methods.

Implementations may include one or more of the following features. The method further including adjusting by the parameter determining circuit the variable time period the sampling gate circuit is open based on the determined sampling time period. The method where the parameter determining circuit determines the sampling time period based on a decay time calculated from the correlation function. The method where the parameter determining circuit determines a data length used for calculating a correlation function, which is based on a decay time calculated from the correlation function. The method where the parameter determining circuit has a determination function, which determines if a calculated correlation function is valid or not based on a coherence factor obtained by the correlation function. The method where the correlation circuit has a judgment function, which determines if a calculated correlation function is valid or not valid based on a plateau level of the correlation function. Implementations of the described techniques may include hardware, a method or process, or computer software on a computer-accessible medium.

Other aspects, features, and techniques will be apparent to one skilled in the relevant art in view of the following detailed description of the embodiments.

BRIEF DESCRIPTION OF THE DRAWINGS

The features, objects, and advantages of the present disclosure will become more apparent from the detailed description set forth below when taken in conjunction with the drawings in which like reference characters identify correspondingly throughout and wherein.

DETAILED DESCRIPTION

Figure 1:
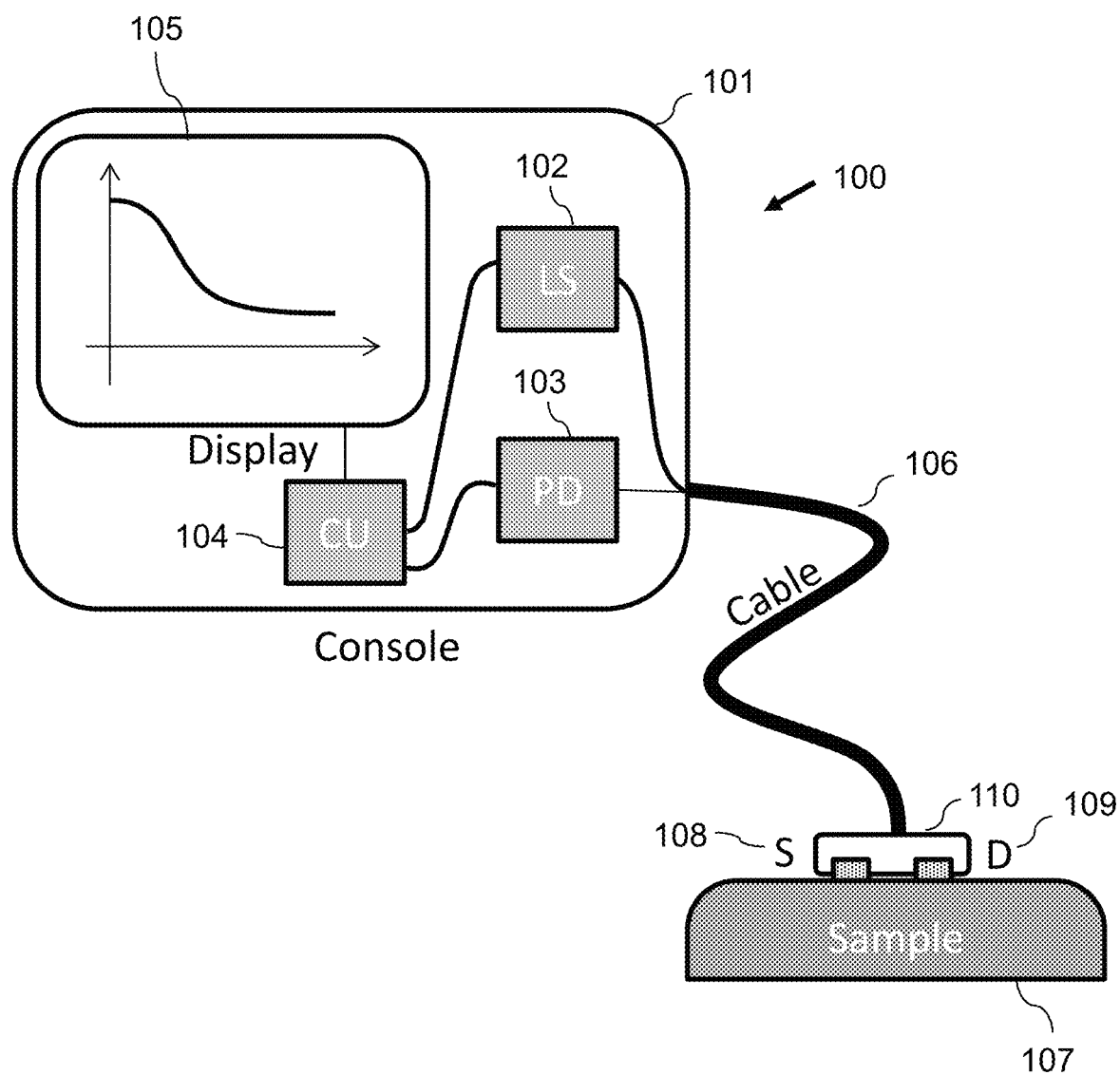
FIG. 1 depicts a graphical representation of a simplified DCS system diagram according to one or more aspects of the present disclosure.

One aspect of this disclosure relates in general to Diffuse Correlation Spectroscopy system for obtaining an autocorrelation function, and more particular, to a correlator and method for controlling a sampling time period and data length used for calculating an autocorrelation function.

As used herein, the terms "a" or "an" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Reference throughout this document to "one embodiment," "certain embodiments," "an embodiment," or similar term means that a particular feature, structure, or characteristic described in connection with the embodiment is included in at least one embodiment. Thus, the appearances of such phrases in various places throughout this specification are not necessarily all referring to the same embodiment. Furthermore, the particular features, structures, or characteristics may be combined in any suitable manner on one or more embodiments without limitation.

Calculation Method for Intensity Autocorrelation Function

Calculating the intensity autocorrelation function, also known as g2(τ), can extract meaningful information and can be calculated in at least a few ways. According to one or more aspects of the present disclosure, the intensity autocorrelation function can be calculated as follows:

$$g_2(\tau) = \frac{\langle I(t)I(t+\tau)\rangle}{\langle I(t)\rangle^2}, \quad (1)$$

where I(t) is a photon count data, τ is a time lag, and the angular brackets < > denote averaging. Since an intensity autocorrelation function is the result of the multiple scattering, we can assume a laser light is in the condition of the collision broadened (Gaussian-Lorentzian light) in the concept of degree of coherence. Then an obtained autocorrelation function is fitted using the following exponential equation:

$$g_2(\tau)_{fit} = \beta \cdot e^{-\frac{\tau}{\tau_D}} + c, \quad (2)$$

where a β is a coherence factor, a τD is a decay time, also known as a time constant, and c is a constant.

In another aspect of the present disclosure, the intensity autocorrelation function can also be calculated according to Wiener-Khinchin theorem, where the Fourier transform of the power spectrum is the autocorrelation function. Since the photon count data I(t) can be varied based on a photon count rate and data length, it is divided by the product of its average over the evaluation time period and data length N for the normalization purpose.

$$I_{Norm}(t) = I(t)/\overline{I(t)}, \quad (3)$$

Then, a power spectrum P(ω) and the intensity autocorrelation function $g_2(\tau)$ are calculated as the following:

$$P(\omega) = F\{I_{Norm}(t)\} \cdot F^*\{I_{Norm}(t)\}, \quad (4)$$

$$g_2(\tau) = F^{-1}\{P(\omega)\}/N, \quad (5)$$

where F represents Fourier transform, * represents complex conjugate, $F^{-1}$ represents inverse Fourier transform, and N represents number of data. This method of calculating an intensity autocorrelation function is also known as FFT.

Exemplary Embodiments

Referring now to the figures, FIG. 1 depicts a graphical representation of a simplified DCS system diagram according to one or more aspects of the present disclosure. System 100 can be configured for presentation of g2(τ) and related parameters. By way of example, system 100 includes a console 101. Console 101 can include a light source 102, light receiving unit 103, control unit 104, and display unit 105.

Light source 102 can be a laser light or any other coherent light with about 10 m coherent length emitted from light source 102. In one or more embodiments, light source 102 can be coupled to a cable 106 which can transfer the laser light from light source 102 to a light sampling unit 110 and further onto sample 107. In one or more embodiment, cable 106 can be an optical fiber or other device to transfer a light signal or information from light source 102 to light sampling unit no. Light sampling unit 110 can include at irradiation point 108 and a detection optical fiber 109. Light from light source 102 penetrates sample 107 by irradiation point and scatter in the sample 107. Part of scattered light from light source 102 can come back to the surface of sample 107 and be detected by detection optical fiber 109 of light sampling unit 110.

Detected light by the detection optical fiber 109 can then be transmitted by cable 106 as an input of detected light to light receiving unit 103 of console 101. In one or more embodiments, light receiving unit 103 can be a photodiode or other detection sensor which receives a light signal from a sampling source. Light receiving unit 103 determines the electrical signal related to the optical intensity and transmits the determined photon signal to control unit 104.

Control unit 104 include a correlator which calculates an intensity autocorrelation function, $g2(\tau)$ using photon signal, and the correlator can also extracts a coherence factor $\beta$ and a decay time $\tau D$ from the intensity autocorrelation function. Calculations from control unit 104 are then transmitted to display unit 105 which can display the $g2(\tau)$ and related parameters, such as $\beta$ values and $\tau$ values extracted from the $g2(\tau)$. In addition to receiving photon signal from light receiving unit 103, Control unit 104 can also control light source 102 such as activating light source 102 or controlling the amount of time the light source 102 is activated.

Figure 2:
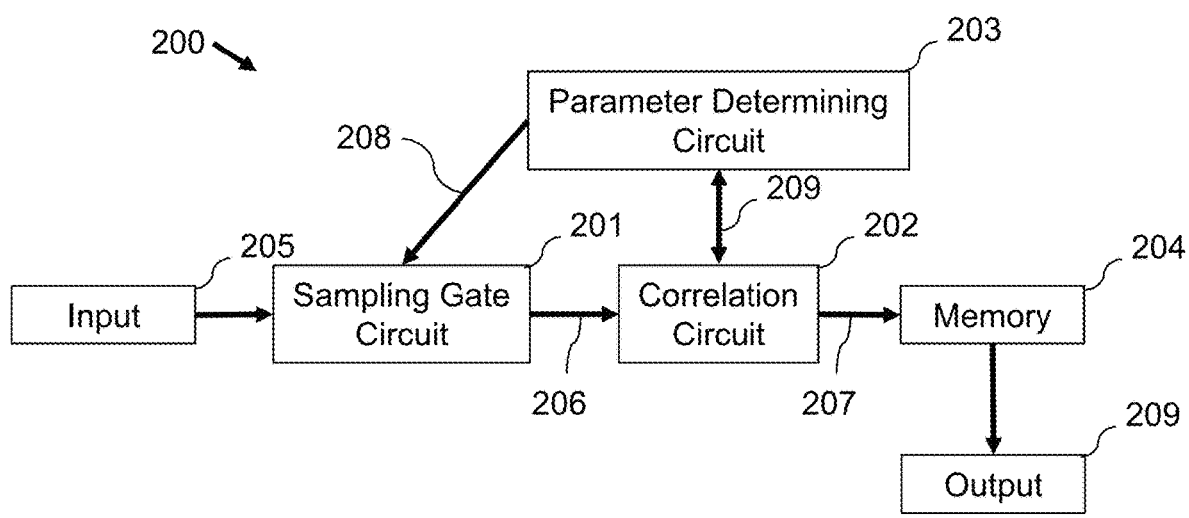
FIG. 2 depicts a graphical representation of a correlator including a variable gate controlling a sampling time for an input signal and a feed-back system according to one or more aspects of the present disclosure.

FIG. 2 depicts a graphical representation of a correlator including a variable gate controlling a sampling time for an input signal and a feed-back system according to one or more aspects of the present disclosure. By way of example, system 100 includes a correlator 200. Correlator 200 can include a sampling gate circuit 201, correlation circuit 202, parameter determining circuit 203, and memory 204.

Photon signal input 205 can be an electrical signal related to the optical intensity obtained from the light receiving unit 103. In one or more embodiment, photon signal input 205 can also be a photon signal from a photodiode or other detection sensor which receives a light signal from a sampling source. Photon signal input 205 from light receiving unit is received by sampling gate circuit 201. Electrical signal from photon signal input 205 can open sampling gate circuit 201 to obtain a light sampling and count the numbers of photons for a variable time period.

Sampling gate output 206 of the sampling gate circuit 201 can be the number of photons received from light receiving unit 103 which is obtained from sample 107. The number of photons received by sampling gate circuit 201 can then be transmitted as sampling gate output 206 to correlation circuit 202.

Correlation circuit 202 can be coupled to or have memory 204. Memory 204 can store the number of photons and calculates intensity autocorrelation function $g2(\tau)$ using a designated data length of a photon signal. In one or more embodiments, correlation circuit 202 can also calculate a decay time $\tau D$ by fitting an exponential function as described in Equation (2). In one or more embodiments, correlation circuit 202 can also calculate a coherence factor $\beta$ by fitting an exponential function as described in Equation (2). The calculated intensity autocorrelation function $g2(\tau)$, the decay time $\tau D$, and the coherence factor $\beta$ are then transferred and stored 207 in memory 204. In one or more embodiments, memory 204 can also be dynamic random access memory (DRAM). The decay time $\tau D$ and the coherence factor $\beta$ calculated by correlation circuit 202 are then transferred to parameter determining circuit 203.

Parameter determining circuit 203 can determine the amount of time the sampling gate circuit 201 can be open to receive photon signal input 205 from light receiving unit 103. In one or more embodiments, parameter determining circuit 203 is a feed-back system that can dynamically determine a time period or sampling time for sampling gate circuit 201. In one or more embodiments, parameter determining circuit 203 determines the sampling time needed and then controls or adjust 208 sampling gate circuit 201 based on the determined results. In one or more embodiments, parameter determining circuit 203 is a feed-back system that can dynamically determine a total data length for correlation circuit 202. In one or more embodiments, parameter determining circuit 203 determines the total data length needed and then controls or adjust 209 correlation circuit 202 based on the determined results. In one or more embodiments, parameter determining circuit 203 is a feed-back system that can dynamically determine in parallel a time period or sampling time for sampling gate circuit 201 and a total data length for correlation circuit 202. According to one or more aspects of the present disclosure parameter determining circuit 203 can transmit controls or adjust 208, 209 signals to the correlation circuit and sampling gate circuit 201 individually. According to one or more aspects of the present disclosure parameter determining circuit 203 can transmit controls or adjust 208, 209 signals to both the correlation circuit and sampling gate circuit 201 in parallel.

According to one or more aspects of the present disclosure when the decay time $\tau D$ is $1\times10^{-5}$ sec, the sampling gate circuit 201 time period can be $1\times10^{-6}$ sec, and when the decay time $\tau D$ is $1\times10^{-4}$ sec, the sampling gate circuit 201 time period can be $1\times10^{-5}$ sec. In correlation circuit 202, the total data length used for calculating $g2(\tau)$ can be adjusted based on the value of decay time $\tau D$. In another aspect of the present disclosure, when the decay time $\tau D$ is $1\times10^{-5}$ sec, the total data length can be 400 msec, and when the decay time $\tau D$ is $1\times10^{-4}$ sec, the total data length can be 200 msec. In correlation circuit 202, the coherence factor $\beta$ can be used for selecting valid $g2(\tau)$. In another aspect of the present disclosure, when the coherence factor $\beta$ of a $g2(\tau)$ is in the range of $0.4<\beta<0.6$, the correlation circuit 202 judges or determines the $g2(\tau)$ is valid for multiple scattering case with randomized polarization. In another aspect of the present disclosure when the constant c of a $g2(\tau)$ is in the range of $0.98<c<1.02$, the correlation circuit 202 judges or determines the $g2(\tau)$ is valid.

Once correlator 200 has stored the calculated intensity autocorrelation function $g2(\tau)$, the decay time $\tau D$, and the coherence factor $\beta$ based on the adjusted sampling time into memory 204 from correlation circuit 202, the data can then be transferred as a output 209 to control unit 104 of the console 101. Control unit 104 can then display obtained data on display unit 105 of console 101. In one or more embodiments, control unit 104 can store data in a storage device instead of displaying the data on display unit 105 or store data in a storage device while displaying the data on a display device 105. In one or more embodiments, control unit 104 can also transmit data to another source such as a storage device local to the device or to another storage device over a network.

Figure 3A:
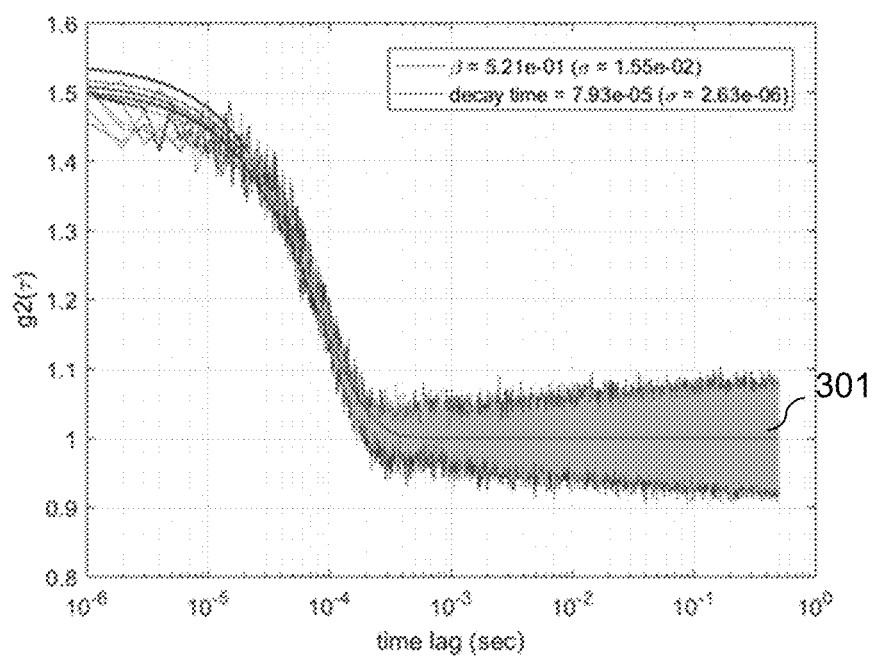
FIG. 3A depicts a graph illustrating exemplary results of intensity autocorrelation functions and fitted exponential curves obtained by using an intralipid sample according to one or more aspects of the present disclosure.
Figure 3B:
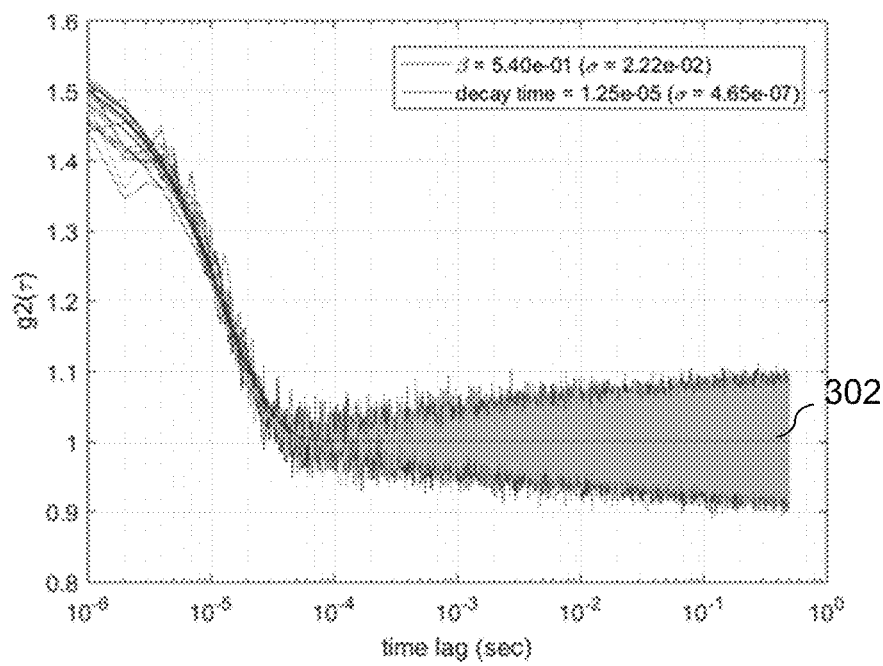
FIG. 3B depicts a graph illustrating exemplary results of intensity autocorrelation functions for static intralipid sample according to one or more aspects of the present disclosure.

FIG. 3A depicts a graph illustrating exemplary results of intensity autocorrelation functions and fitted exponential curves obtained by using an intralipid sample according to one or more aspects of the present disclosure. FIG. 3B depicts a graph illustrating exemplary results of intensity autocorrelation functions for static intralipid sample according to one or more aspects of the present disclosure.

The horizontal axis represents a time lag $\tau$ in the unit of second and the vertical axis represents a normalized intensity autocorrelation function, $g2(\tau)$. FIGS. 3A and 3B contain 10 of $g2(\tau)$, which are calculated by separately measured photon signals, and 10 of fitted curves, which are exponentially fitted by using Equation (2). FIGS. 3A and 3B show averaged coherence factor $\beta$ with standard deviation value using 10 data, and averaged decay time $\tau D$ with standard deviation value using 10 data. Also, a plateau level 301, 302 are a flat region of $g2(t)$ illustrated on the right side of FIG. 3A and FIG. 3B. Plateau level 301, 302 vertical values is around 1 because of normalization. In both graphs, the distance between a source fiber and a detector fiber was 30 mm. To make the averaged decay time $\tau D$ different, the Intralipid sample was static in FIG. 3A, and the Intralipid sample was flowed with 3.0 mL/min in FIG. 3B. Then, the averaged coherence factors $\beta$ for both graphs are almost same, but the averaged decay times $\tau D$ are different each other. The sampling time was 1 μsec and the total data length used for calculating intensity autocorrelation functions was 1 sec. Since the FFT based technique was used for calculating $g2(\tau)$, the $g2(\tau)$ is flipped at 0.5 sec and both FIGS. 3A and 3B only show $g2(\tau)$ until 0.5 sec. For the exponential fitting, data points from $1 \times 10^{-6}$ sec to 0.5 sec were used. The coefficient of variation of decay time $\tau D$ in FIG. 3A was 0.03, and the one in FIG. 3B was 0.04 with using the sampling time of 1 μsec and the total data length of 1 sec.

According to one or more aspects of the present disclosure, to provide a correlator 200 with a function using less size of memory 204, the sampling time and the total data length used for calculating $g2(\tau)$ can be controlled.

Figure 4A:
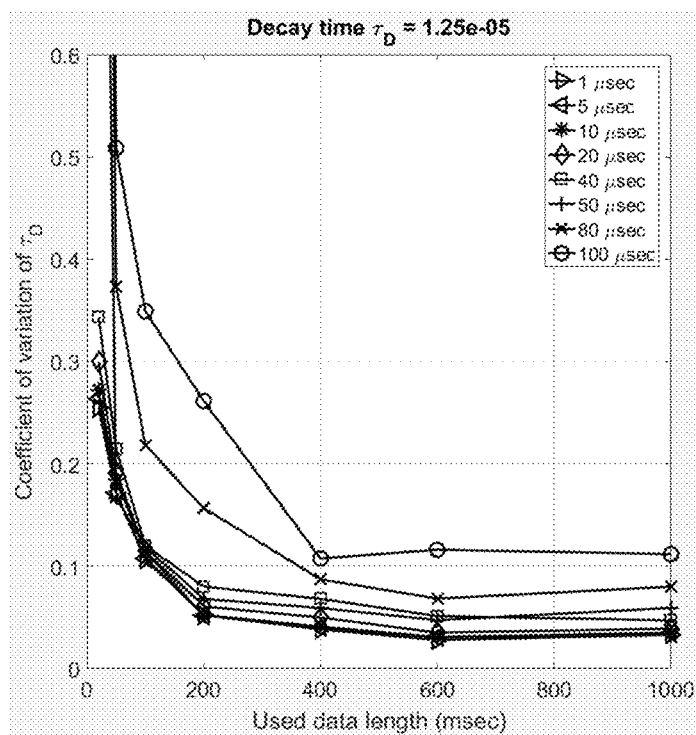
FIGS. 4A and 4B depicts graphs illustrating the relationship between coefficient of variation of τD depending on used data length and sampling time for static intralipid sample according to one or more aspects of the present disclosure.
Figure 4B:
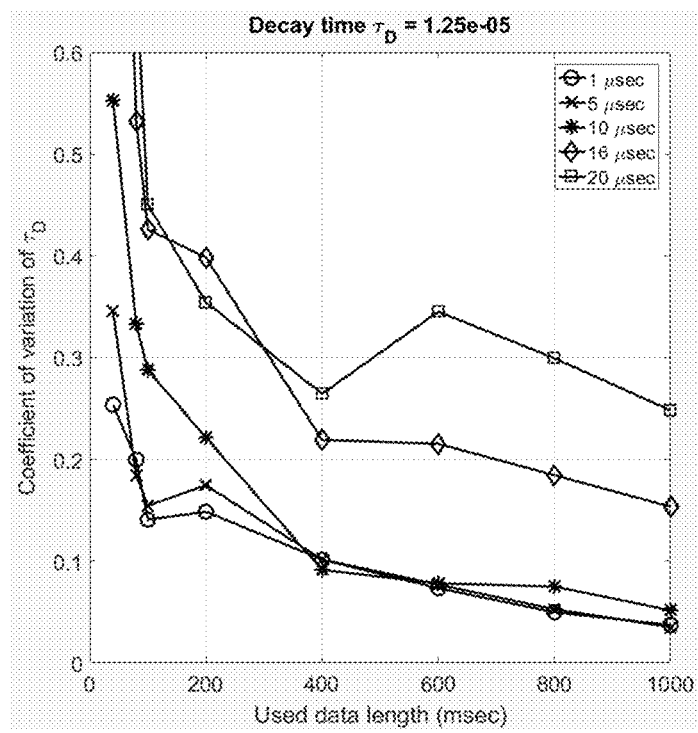

FIGS. 4A and 4B depicts graphs illustrating the relationship between coefficient of variation of $\tau D$ depending on used data length and sampling time for intralipid sample according to one or more aspects of the present disclosure.

The horizontal axis represents the used data length in the unit of msec, and the vertical axis represents the coefficient of variation of $\tau D$. The coefficient of variation of $\tau D$ is calculated by using 10 of $g2(\tau)$, which are calculated by separately measured photon signals. The $g2(\tau)$s were obtained by using an intralipid sample of 0.0625% concentration. The FIG. 4A is the result of using the static intralipid sample with the averaged decay time $\tau D$ of 7.93e-05, and FIG. 4B is the result of using the 3.0 mL/min flowed intralipid sample with the averaged decay time $\tau D$ of 1.25e-05.

According to one or more aspects of the present disclosure, in the case of $\tau D=7.93e-05$ sec, when the target of coefficient of variation is 0.1, the sampling time can be increased to 50 μsec which is equivalent to 0.6 times of $\tau D=7.93e-05$ sec, and the used data length can be reduced to 200 msec which is equivalent to 2.5e03 times of $\tau D=7.93e-05$ sec. In the case of $\tau D=1.25e-05$ sec, when the target of coefficient of variation is 0.1, the sampling time can be increased to 10 μsec which is equivalent to 0.8 times of $\tau D=1.25e-05$ sec, and the used data length can be reduced to 400 msec which is equivalent to 3.2e04 times of $\tau D=1.25e-05$ sec.

Since the required memory size for calculating $g2(\tau)$ can be characterized by the division of the total data length with the sampling time, reducing the total data length and increasing the sampling time reduces the memory size needed. To identify how much the sampling time and the total data length can be adjusted, the decay time $\tau D$ can be the base. According to one or more aspects of the present disclosure, when the $\tau D$ is about 7.93e-05 sec, the sampling time can be 0.6×$\tau D$, and the total data length is 2.5e03×$\tau D$. When the $\tau D$ is about 1.25e-05 sec, the sampling time can be 0.8×$\tau D$, and the total data length is 3.2e04×$\tau D$.

The reason why the case of $\tau D=7.93e-05$ sec can reduce the used data length more than the case of $\tau D=1.25e-05$ is that the $g2(\tau)$ has a flat region in smaller time lag. Then, the required sampling time and the total used length can be adjusted depending on where the averaged decay time is.

Figure 5:
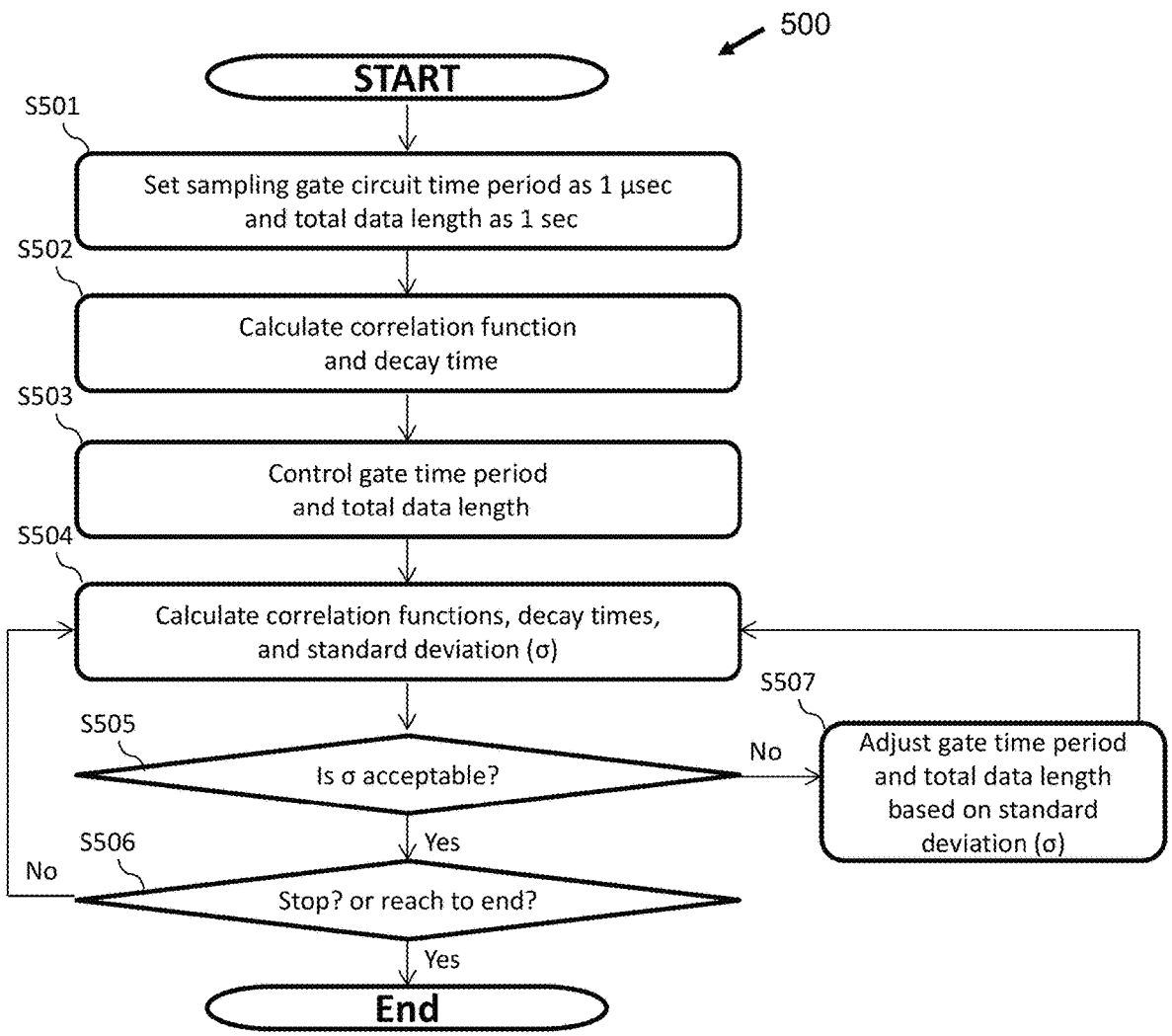
FIG. 5 depicts a graphical representation of various sampling steps for controlling a sampling gate circuit and the total data length used for calculating an intensity autocorrelation function according to one or more aspects of the present disclosure.

FIG. 5 depicts a graphical representation of various sampling steps for controlling a sampling gate circuit and the total data length used for calculating an intensity autocorrelation function according to one or more aspects of the present disclosure. Process 500 may be employed for controlling a sampling gate circuit 201, 202, and 203 of correlator 200. Process 500 may be performed by a system or device such as system 100 of FIG. 1.

In one or more embodiments, the process 500 is initiated by setting sampling gate circuit 201 with a predetermined sampling period and total data length in step S501. For example, sampling time can initially be 1 μsec and total data length can initially be 1 sec prior to analyzing sample 107. The initial sampling time and total data length parameters are used for an initial run of obtaining a photon signal, and parameter values can be set as different values depending on a sample type.

At step S502, correlation circuit 202 calculates an intensity autocorrelation function using data obtained from the initial run at step S501. Correlation circuit 202 can also calculates a decay time $\tau D$, which is obtained by fitting an exponential equation. In step S502, the coherence factor $\beta$ also can be used for selecting valid $g2(\tau)$. The decay time $\tau D$ and the coherence factor $\beta$ calculated by correlation circuit 202 are then transferred to parameter determining circuit 203.

At step S503, parameter determining circuit 203 determines a time period or sampling time for sampling gate circuit 201 and the total data length for correlation circuit 202. Parameter determining circuit 203 then adjusts or controls sampling gate circuit 201 sampling time and the total data length for correlation circuit 202 based on the decay time $\tau D$ value obtained by the initial run at step S502. For example, when the decay time is 1.25e-05 sec, the sampling time can be set to 10 μsec which is equivalent to 0.8 times of the averaged decay time, and the used data length can be set to 400 msec which is equivalent to 3.2e04 times of the averaged decay time.

At step S504, correlation circuit 202 continues calculating intensity autocorrelation functions using the parameters controlled in step S503. Correlation circuit 202 also continues calculating decay times $\tau D$ and coherence factors $\beta$ of the intensity autocorrelation functions for parameter determining circuit 203. When the number of decay times $\tau D$ and coherence factors $\beta$ reach to a designated number, the correlator circuit 202 defines standard deviation $\sigma$ of decay times, and coefficients of variation of decay times.

At step S505, the parameter determining circuit 203 determines if the standard deviation $\sigma$ of decay times $\tau D$, or the coefficient of variation of $\tau D$ is acceptable or not based on a predetermined threshold. If yes, process 500 proceeds to step S506 and if no, process 500 proceeds to step S507.

In step S507, the parameter determining circuit 203 adjusts the sampling time period and the total data length based on the standard deviation σ of decay times τD, or the coefficient of variation of τD and the process 500 proceeds back to step S504. For example, the gate time period may decrease by 1 μsec, or the total data length may increase by 10 msec.

In step S506, correlation circuit 202 determines if this flow is stopped or not. This flow can be stopped after a predetermined cycle is ended, or stopped by manually. If yes, it goes to the end of this flow and if no, it goes back to step S504.

Any methods and/or data of the present disclosure, such as the correlator or methods for controlling a sampling time period and data length used for calculating an autocorrelation function as discussed herein, may be stored on a computer-readable storage medium. A computer-readable and/or writable storage medium used commonly, such as, but not limited to, one or more of a hard disk (e.g., the hard disk, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM"), a DRAM, a read only memory ("ROM"), a storage of distributed computing systems, a memory card, or the like (e.g., other semiconductor memory, such as, but not limited to, a non-volatile memory card, a solid state drive, SRAM, etc.), an optional combination thereof, a server/database, etc. may be used to cause a processor, such as, the processor or CPU of the aforementioned computer to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

The above described devices, systems, and methods can be implemented by supplying one or more computer-readable media having stored therein computer-executable instructions for realizing the above described operations to one or more computer devices that are configured to read the computer-executable instructions and execute them. In this case, the system or devices perform the operations of the above-described embodiments when executing the computer-executable instructions. Also, an operating system on the one or more systems or devices may implement the operations of the above described embodiments. Thus, the computer-executable instructions or the one or more computer-readable media storing the computer-executable instructions or the one or more computer-readable media storing the computer-executable instructions thereon constitute an embodiment.

While this disclosure has been particularly shown and described with references to exemplary embodiments thereof, it will be understood by those skilled in the art that various changes in form and details may be made therein without departing from the scope of the claimed embodiments.

What is claimed is:

1. A diffuse correlation spectroscopy (DCS) system, comprising:
    a light source configured to emit coherent light suitable for propagation through a sample;
    a detector configured to detect at least part of the coherent light after propagation through the sample, and to output an electrical signal corresponding to a photon count of the detected coherent light;
    a single sampling gate circuit which is open to receive the electric signal from the detector during a variable time period and provides a data sample having a data length corresponding to the photon count;
    a correlation circuit which calculates a correlation function from the data sample provided from the single sampling gate circuit;
    a parameter determining circuit which determines a sampling time period based on one or more of a decay time and a coherence factor of the correlation function and feeds back the sampling time period to the single sampling gate circuit; and
    a memory used to store data of the correlation function and the data sample,
    wherein the parameter determining circuit reduces the data length of the data sample to be stored in the memory and increases the sampling time period to be used by the single sampling gate circuit based on a value of the one or more of the decay time and the coherence factor, such that a size of the memory used to store the data is reduced.

2. The DCS system according to claim 1, wherein the parameter determining circuit adjusts the variable time period during which the single sampling gate circuit is open based on the determined sampling time period.

3. The DCS system according to claim 2, wherein the single sampling gate circuit provides a second data sample to the correlation circuit.

4. The DCS system according to claim 1, wherein the parameter determining circuit determines the sampling time period based on a decay time calculated from the correlation function.

5. The DCS system according to claim 1, wherein the parameter determining circuit determines a data length used to calculate the correlation function, which is based on a decay time calculated from the correlation function.

6. The DCS system according to claim 1, wherein the parameter determining circuit has a determination function, which determines if a calculated correlation function is valid or not based on a coherence factor obtained by the correlation function.

7. The DCS system according to claim 1, wherein the correlation circuit has a determination function, which determines if a calculated correlation function is valid or not valid based on a plateau level of the correlation function.

8. The DCS system according to claim 1, wherein the correlation circuit further calculates the decay time of the correlation function, by fitting the correlation function to an exponential equation.

9. A method of controlling a diffusing wave spectroscopy (DCS) system to calculate a correlation function, comprising:
- emitting coherent light from a light source towards a sample, the coherent light being suitable for propagation through the sample;
- detecting at least part of the coherent light after propagation through the sample, and outputting an electrical signal corresponding to a photon count of the detected coherent light;
- controlling to open a single sampling gate circuit to receive the electric signal during a variable time period and providing a data sample having a data length corresponding to the photon count;
- calculating by a correlation circuit a correlation function from the data sample provided from the single sampling gate circuit;
- determining by a parameter determining circuit a sampling time period based on one or more of a decay time and a coherence factor of the correlation function and feeding back to the single sampling gate circuit the sampling time period; and
- storing data of the correlation function and the data sample in a memory,
- wherein the determining by the parameter determining circuit includes reducing the data length of the data sample to be stored in the memory and increasing the sampling time period to be used by the single sampling gate circuit based on a value of the one or more of the decay time and the coherence factor, such that a size of the memory used to store the data is reduced.

10. The method of claim 9, further comprising adjusting by the parameter determining circuit the variable time period during which the single sampling gate circuit is open based on the determined sampling time period.

11. The method of claim 10, wherein the single sampling gate circuit provides a second data sample to the correlation circuit.

12. The method of claim 9, wherein the parameter determining circuit determines the sampling time period based on a decay time calculated from the correlation function.

13. The method of claim 9, wherein the parameter determining circuit determines a data length used for calculating a correlation function, which is based on a decay time calculated from the correlation function.

14. The method of claim 9, wherein the parameter determining circuit has a determination function, which determines if a calculated correlation function is valid or not based on a coherence factor obtained by the correlation function.

15. The method of claim 9, wherein the correlation circuit has a judgment function, which determines if a calculated correlation function is valid or not valid based on a plateau level of the correlation function.

* * * * *